United States Patent [19]

Konno et al.

[11] Patent Number: 4,842,577
[45] Date of Patent: Jun. 27, 1989

[54] PLASTER STRUCTURAL ASSEMBLY FOR IONTOPHORESIS

[75] Inventors: Yutaka Konno; Mitsuo Mitomi; Takashi Sonobe, all of Shizuoka; Shumpei Yamaguchi, Tokyo, all of Japan

[73] Assignee: Yamanouchi Pharmaceutical Co., Ltd., Tokyo, Japan

[21] Appl. No.: 109,083

[22] Filed: Oct. 16, 1987

[30] Foreign Application Priority Data

Oct. 20, 1986 [JP] Japan ................... 61-250364

[51] Int. Cl.⁴ .............................................. A61N 1/30
[52] U.S. Cl. ......................................... 604/20; 128/803
[58] Field of Search ................... 204/299 R; 604/20; 128/789, 802, 803

[56] References Cited

U.S. PATENT DOCUMENTS

| 4,164,226 | 8/1979 | Tapper | 128/798 X |
|---|---|---|---|
| 4,325,367 | 4/1982 | Tapper | 604/20 |
| 4,383,529 | 5/1983 | Webster | 604/20 |
| 4,557,723 | 12/1985 | Sibalis | 128/798 X |
| 4,722,726 | 2/1988 | Sanderson et al. | 128/798 X |
| 4,731,049 | 3/1988 | Parsi | 604/20 |
| 4,747,819 | 5/1988 | Phipps et al. | 128/798 X |

Primary Examiner—John F. Niebling
Assistant Examiner—John S. Starsiak, Jr.
Attorney, Agent, or Firm—Burgess, Ryan & Wayne

[57] ABSTRACT

A novel plaster structural assembly is provided for iontophoresis wherein the assembly is comprised of an electrode layer and a medicament-containing layer in which a water supplying layer is disposed between the electrode layer and the medicament-containing layer with a sealing cover disposed on the outside of the electrode layer. A method for using the structural assembly for iontophoresis is also provided.

5 Claims, 3 Drawing Sheets

PLASTER STRUCTURAL ASSEMBLY FOR IONTOPHORESIS

FIELD OF THE INVENTION

This invention relates to a novel plaster structural assembly for iontophoresis.

BACKGROUND OF THE INVENTION

An iontophoresis is a method of ionizing a medicament by passing electric current through the medicament thereby permitting absorption of the medicament in an ionized state through the skin. The method also involves attaching a medicament to one of a cathode or an anode, mounting both electrodes on the skin with a definite interval, and introducing an electric current to the electrodes from an electric current generator by a leading wire is generally employed (see, e.g., Japanese Patent Application (OPI) Nos. 156475/85, 188176/85, 31169/86, etc.). (The term "OPI" as used herein means an "unexamined published application").

In this case, a medicament which is positively ionized is fixed to an anode and a medicament which is negatively ionized is fixed to a cathode. In these electrodes, as the electrode which does not carry a medicament, a conductive gel layer permeated with sodium chloride is usually used. The absorption of a medicament by the iontophoresis is generally better as the electric current and voltage applied are higher. However, when a high electric current of high voltage is passed through the skin for a long period of time, a skin injury such as rubescene, burning, occurs. This sometimes reduces the absorption of medicament through the skin as well and complicates the administration of medicament by iontophoresis. For solving these problems, an iontophoresis method employing a system of passing high frequency pulse electric current was recently proposed (see, Japanese Patent Application (OPI) No. 31169/86).

Now, the absorption extent of medicament by iontophoresis is influenced by a plaster structural assembly containing medicament in addition to the intensity of electric current and the time for passing the electric current. As a conventional plaster structural assembly for iontophoresis, there are known a structural assembly wherein an electrode is covered by absorbent cotton impregnated with medicament, a structural assembly wherein a liquid containing medicament is infused into a tubular cap closely adapted to the skin and an electrode is connected to the cap, and a structural assembly wherein a conductive electrode layer and a medicament-containing conductive gel layer are simply laminated.

However, these plaster structural assemblies have disadvantages in that the absorption of medicament is insufficient and also the absorption decreases with the passage of time. Also, the first two plaster structural assemblies are inconvenient for handling and hence there are problems for practical uses.

SUMMARY OF THE INVENTION

The object of this invention is, therefore, to overcome the difficulties of conventional structural assemblies and to provide a practical plaster structural assembly which is excellent in skin safety and greatly increases the utilization efficiency of medicament.

That is, the invention is a novel plaster structural assembly for iontophoresis comprising an electrode layer and a medicament-containing layer, wherein a water supplying layer (composed of a water-containing layer 2 and/or a water-containing self adhesive layer 3) is formed between an electrode layer 4 and a medicament-containing layer 1 and further a sealing cover 5 is formed at the outside of the electrode layer 4.

DETAILED DESCRIPTION OF THE INVENTION

Figure 1:
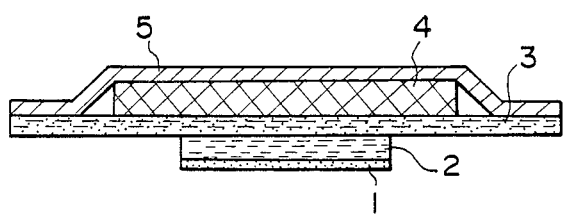
FIG. 1 is a cross-sectional view showing the plaster structural assembly of this invention obtained in Example 1.

The invention is described in detail by referring to the accompanying drawings.

The plaster stuctureal assembly of this invention has the structures as shown in FIG. 1 to FIG. 4. In these figures, numeral 1 is a medicament-containing layer, 2 a water-containing layer, 3 a water-containing self adhesive layer, 4 an electrode, 5 a sealing cover, and 6 (FIG. 4) an electrolyte capsule.

The medicament-containing layer 1 is a thin layer composed of an element having high skin adhesivity and electrical conductivity containing a medicament.

As the skin-adhesive material, a hydrophilic resin or a high molecular compound is used. As the hydrophilic resin, there are acrylic resins such as polyacrylamide, polyacrylic acid, and the alkali metal salts or esters thereof, vinylic resins such as polyvinylpyrrolidone, polyvinyl alcohol, polyvinyl ethyl ether, and the copolymers thereof, natural polysaccharides such as traganth gum, caraya gum, etc. Also, as the high molecular compound, there are methyl cellulose, hydroxypropyl cellulose, hydroxypropylmethyl cellulose, hyaluronic acid, and the alkali metal salts thereof.

For preparing the medicament-containing layer using the aforesaid material, the material is kneaded with a solution of a medicament. In this case, they are properly compounded with water, polyethylene glycol, propylene glycol, glycerol, etc., as a soft plasticizer and also sodium chloride, sodium carbonate, phosphoric acid, sodium citrate, etc., as an electrolyte for imparting electrical conductivity.

As a liquid for dissolving medicament, a buffer liquid composed of phosphoric acid, citric acid, etc., is usually used but an aqueous solution of an organic amine or mineral acids such as hydrochloric acid, etc., an aqueous citric acid solution, etc., may be used singly or as a combination thereof according to the nature of a medicament.

Also, as a medicament-containing layer, a material such as cotton, filter paper, membrane filter, etc., impregnated with a medicament-containing solution imparted with electric conductivity can be used.

The medicament-containing layer is prepared to an extent capable of keeping the self form-retaining property and is spread in a film form or sheet form. The thickness thereof is preferably from 0.1 mm to 1.0 mm, particularly preferably from 0.2 mm to 0.5 mm. If the thickness is too thick, it sometimes happens that good absorption of medicament through the skin is not obtained.

In regard to the concentration of medicament in the medicament-containing layer, the application of a concentration incline give good results. That is, by using a medicament-containing layer of a laminate layer type that the layer which is brought into contact with the skin has the lowest concentration of medicament and layers each having higher concentration are disposed in succession to provide a concentration incline can give stable and high absorption value through the skin.

There is no particular restriction on the size (area) of the medicament-containing layer but the area is suitable from about ½ to about ⅓ of the area of the water-containing self adhesive layer 3.

As the medicament, an ionic medicament having a small distribution coefficient for oil is mainly used. Examples thereof are shown as the following medicament groups although the invention is not limited to these medicaments.

Antitussive Expectorant Agent

Sodium chromoglycate and Ketotifen fumarate

Bronchodilator

Formoterol fumarate

Analgesics

Narbuphine hydrochloride, Pentazocine lactate, Diclofenac sodium.

Cardiac

Dopamine hydrochloride.

Tranquilizers

Perphenazine and Phenothiazine.

Antibiotics

Cefotetan disodium, Dibekacin sulfate, Amikacin sulfate, Netilmicin sulfate, and Sisomicin sulfate.

Cytostatics

Adriamycin, Mitomycin C, Breqmycin hydrochloride, Lentinan, Picibanil, Vincristine sulfate, Cisplatin Circulating Function Improving Agent Nicardipine hydrochloride.

Cerebral metabolism activator

Nicametate citrate, Meclofenoxate hydrochloride, Lisuride maleate, Calcium homopantothenate Gout Treating Agent Allopurinol Peptides LHRH, Enkephalin, Endorphin, Interferon, Insulin, Carcitonin, TRH, NT-36 (chemical name: N-[[(s)-4-oxo-2-azetidinyl]carbonyl]-L-histidyl-L-prolinamide), Oxytocin, Liprecin, Vasopressin, Glucagon, Pituitary hormones (e.g., HGH, HMG, HCG, Desmopressin acetate, etc.,), Follicle luteoids.

Then, the water supplying layer (composed of a water-containing layer 2 and/or a water-containing self adhesive layer 3) is disposed between the medicament-containing layer 1 and the electrode layer 4.

Figure 3:
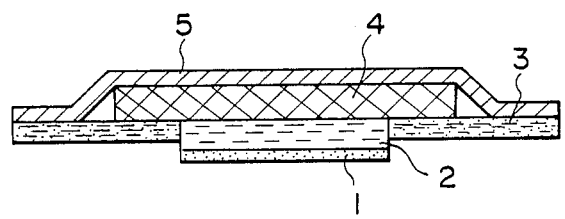
FIG. 3 is a cross-sectional view showing the plaster structural assembly of this invention obtained in Example 2.
Figure 4:
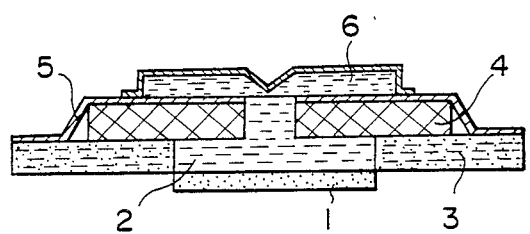
FIG. 4 is a cross-sectional view showing a plaster structural assembly equipped with an electrolytes capsule.

The water supplying layer is composed of a water-containing layer 2 which is composed of water retentive fibers such as cotton, sponge, cellulose triacetate, etc., and a water-containing self adhesive layer 3 which is composed of the hydrophilic resin or high molecular compound (as described hereinbefore) imparted with electrical conductivity. The water-containing layer 2 and the water-containing self adhesive layer may be used singly for the water supplying layer or both layers may be used as the laminate thereof. Furthermore, as shown in FIG. 3 and FIG. 4, the water-containing layer 2 may be disposed at the portion in contact with the medicament-containing layer 1 and the water-containing self adhesive layer 3 may be disposed at the surrounding portion.

The size (area) of the water supplying layer is the same as the area of the medicament-containing layer or larger than the latter area. When the water supplying layer of the aforesaid laminate type is employed, it is preferred that at least the water-containing self adhesive layer 3 is larger than the area of the medicament-containing layer and covers the whole surface of the electrode layer, whereby the direct contact of the electrode layer with the skin is prevented to reduce the occurrence of skin injury. The thickness of the water-containing self adhesive layer 3 is preferably from 1 mm to 5 mm from the view point of preventing the occurrence of skin injury.

The water-containing layer 2 may previously contain an electrolyte solution or may be filled up with an electrolyte solution at the application thereof to the skin. In the case of impregnating the water-containing layer with an electrolyte solution, it is convenient to employ a constriction that a capsule 6 containing an electrolyte solution is formed on the upper portion of the plaster structural assembly and a thin film such as aluminum foil, etc., disposed between the capsule 6 and the water-containing layer 2 is collapsed at the application of the assembly to impregnate the water-containing layer 2 with the electrolyte.

Then, an electrode layer 4 is an electric current dispersing material usually composed of a conductive rubber, a resin film, a carbon film, or a metal foil such as aluminum foil, etc. It is preferred that the area of the electrode is from 2 to 3 times the area of the medicament-containing layer. By employing the aforesaid construction, the current density per unit area can be reduced to reduce the occurrence of skin injury at the applied portion and also accelerate the absorption of medicament through the skin.

The sealing cover 5 is a water impermeable skin adhesive sheet. The cover is usually composed of flannel or cotton cloth impregnated with vaseline or an adhesive plastic tape. etc. The sealing cover may have an area of covering the whole surface of the electrode layer and further cover the surrounding portion of the electrode layer.

The plaster structural assembly of this invention has usually a waterproof releasing liner on the side thereof which is brought into contact with the skin and is used for practical purpose in a sealed state. Where a water-decomposable medicament is used, it is better that the medicament-containing layer 1 and the water-containing layer 2 are in a dried state and a capsule 6 containing an electrolyte solution is formed on the water-containing layer 2 as shown in FIG. 4.

As described above, the plaster structural assembly of this invention is novel in the point of disposing a water supplying layer and a sealing cover and by forming these layers, a sufficient supply of water in the medicament-containing layer can be attained to give efficient absorption of the medicament through the skin. Also, the employment of the medicament-containing layer having the gradient concentration of medicament and the employment of the water-containing self adhesive layer 3 over the whole surface of the electrode layer are more useful for increasing the absorption of medicament and skin safety at the application of the plaster structural assembly of this invention.

When using the plaster structural assembly of this invention, the structural assembly and a counter electrode are mounted on the skin with an interval of at least few millimeters and a desired electric current is passed through the electrode layer 4 and the counter electrode 20 by leading wires from an electric current generator.

The plaster structural assembly of this invention is explained by referring to the following examples.

EXAMPLE 1

A definite amount of a medicament was dissolved in a liquid, the solution was kneaded with polyacrylamide, and a medicament-containing layer 1 having 2.8 $cm^2$ in area and 0.4 mm in thickness was prepared. A water-containing layer 2 composed of a cotton cloth (2.8 $cm^2$ in area and 0.2 mm in thickness) impregnated with 400 $\mu l$ of water imparted with electrical conductivity was laminated on the medicament-containing layer 1. Furthermore, a circular water-containing self adhesive layer 3 composed of a polyacrylamide gel (8.5 $cm^2$ in area and 0.4 mm in thickness, containing 80% water) was laminated thereon. Then, an electrode layer 4 having the same area as above was disposed on the water-containing self adhesive layer 3 and further a sealing cover 5 composed of a sheet having an adhesive layer of natural rubber adhesive (made by, Marusho Kinzoku Haku K.K.) was covered on the outer surface thereof to provide a plaster structural assembly covered by the sealing cover 5 (see, FIG. 1).

EXAMPLE 2

A circular hole of 2.8 $cm^2$ in area was formed at the center of a circular polyacrylamide layer (8.5 $cm^2$ in area and 0.4 mm in thickness, containing 80% water) and in the hole of the water-containing adhesive layer 3 thus formed were mounted a medicament-containing layer 1 and a water-containing layer 2 prepared by the same manners as in Example 1. Then, an electrode layer 4 and a sealing cover 5 were disposed thereon as in Example 1 to provide the plaster structural assembly (see, FIG. 3).

EXAMPLE 3

Figure 2:
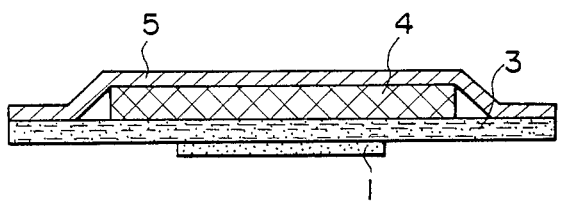
FIG. 2 is a cross-sectional view showing the plaster structural assembly of this invention obtained in Example 3.

The plaster structural assembly of the example was prepared by the same manner as Example 1 except that the water-containing layer 2 was omitted (see, FIG. 2).

Then, using the plaster structural assemblies of this invention prepared as above, the absorption effect of medicament by iontophoresis was measured by the following experimental conditions. The results are explained by comparing with conventional administration modes of medicament for iontophoresis.

Experimental Condition

Medicament: Salmon carcitonin having a molecular weight of about 3,400 (hereinafter, is referred to a sCT)

Animal: Guinea pigs

Measurement Method: The reduction effect of plasma calcium concentration by the absorption of sCT through the skin was measured. The measurement of the plasma calcium concentration was performed using Calcium Meter Type CA-30 (made by Jokosha K.K.).

Administration Method: In experiment Examples 1 to 3 are shown the administration methods by plaster structural assemblies of this invention and in Comparison Examples 1 to 3 are shown by administration methods by an subcutaneous injection method, a solution cap method, and a conventional plaster assembly method (without the water supplying layer and sealing cover).

Comparison Example 1 (Subcutaneous injection method, sCT 5 IU/kg)

After injection of sCT solution (an aqueous sCT solution of 0.0001 M citric acid) into the back portion of a guinea pig, the blood was taken at every specified time (at minutes to 9 hours) and the concentration of calcium was measured.

Comparison Example 2 (Solution cap method, sCT 100 IU/kg)

In a McIlvaine buffer of pH 4.0 was dissolved sCT to provide a solution of IU/ml of sCT. Then, about 2 ml of the solution was placed in an acrylic resin cap (2.8 $cm^2$ in area and 1 cm in height, equipped with an electrode at the inside of the cap) previously mounted on the skin of abdomen of a guinea pig and an electric current of 12 volts and 40 KHz was passed for 1 to 12 hours. In addition, as a cathode, an acrylamide gel sheet prepared by kneading with an aqueous sodium chloride solution was used. The blood was taken at every specified time and the concentration of calcium was measured.

Comparison Example 3 (Conventional plaster assembly, sCT 100 IU/kg)

A sCT-containing gel sheet was prepared so that the dose of sCT to guinea pig became 100 IU/kg and was placed on a conductive silicone rubber side of an anode layer (2.8 $cm^2$ in area, stainless steel foil/conductive silcone rubber). The anode layer was mounted on the skin of a guinea pig, an electric current of 5 mA and 40 KHz was passed therethrough, the blood was taken at every specified time, and the concentration of calcium was measured.

Experimental Example 1 (sCT 20 IU/kg)

An aqueous 1% gelatin solution of 0.0001 M citric acid was used for dissolving sCT and the plaster structural assembly shown in Example 3 having the medicament-containing layer prepared by the aqueous solution of sCT so that the doses of sCT to guinea pig became 20 IU/kg was mounted on the skin of a guinea pig. After passing an electric current of 10 mA and 40 KHz for from 1 to 9 hours, the blood was taken at every specified time and the concentration of calcium was measured.

Experimental Example 3 (sCT 10 IU/kg)

The concentration of calcium was measured as in Experiment Example 2 using the plaster structural assembly of Example 1 having the medicament-containing layer prepared so that the doses of sCT became 10 IU/kg.

Results

Figure 5:
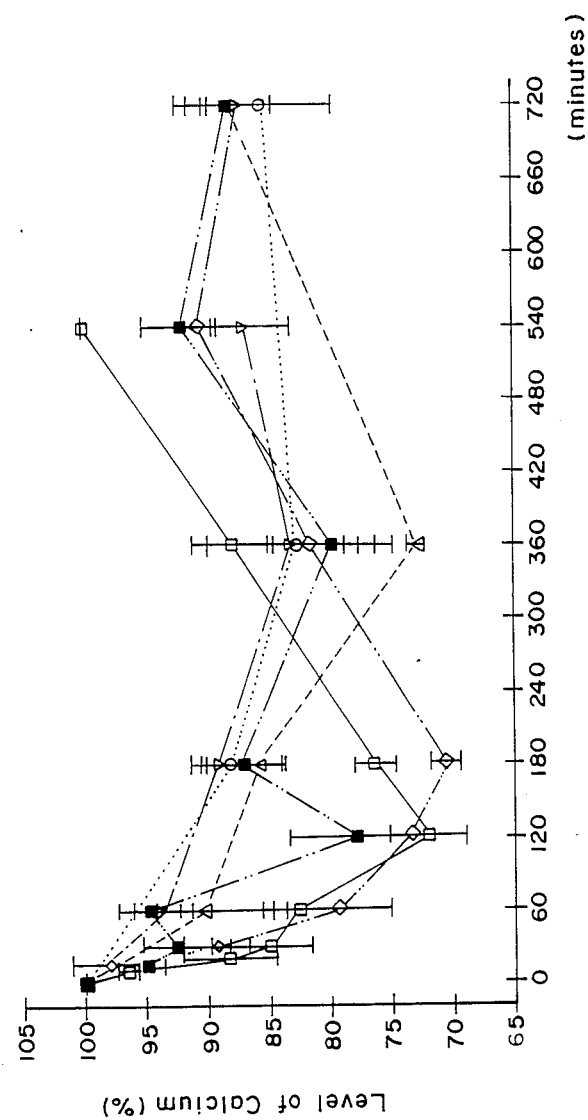
FIG. 5 shows plasma calcium level versus time in guinea pigs after subcutaneous and iontophoretic administration.

The calcium level in the blood plasma every specified time is shown in FIG. 5 and the relative reduction ratio of calcium to the intravenous injection of 5 IU/kg is shown in the following table.

TABLE 1

| Example | sCT dose (IU/kg) | Reduction Ratio of Ca in Blood (%)* | State of Skin |
| --- | --- | --- | --- |
| Comparison Example 1 | 5 | 100 | — |
| Comparison Example 2 | 100 | 4.2 | Normal |
| Comparison Example 3 | 100 | 5.8 | Rubescene occured after 12 hs. since the application |
| Experimental 1 | 20 | 20.3 | Normal |
| Experimental 2 | 20 | 33.0 | Normal |
| Experimental 3 | 10 | 48.4 | Normal |

*From the curve of plasma calcium level versus time taken during 9 hours after the application of the plaster structural assembly, the medical effect strength area (unit % min.) was determined and also the reduction ratio of plasma calcium level to the case of the subcutaneous injection of 5 IU/kg was calculated by the following equation.

Reduction ratio (%) of calcium in blood $= \frac{A \times 5}{B \times C} \times 100$ A: Medical effect strength area in the administration through the skin.
B: Medical effect strength area in subcutaneous injection.
C: Dose of sCT at the iontophoretic administration through the skin.

What is claimed is:

1. A plaster structural assembly for iontophoresis comprising an electrode layer and a medicament containing layer, wherein a water supplying layer is disposed between the electrode layer and the medicament-containing layer and further a sealing cover is formed at the outside of the electrode layer, said water supplying layer composed of water and water retentive fibers.

2. A plaster structural assembly for iontophoresis comprising an electrode layer and a medicament containing layer, wherein a water supplying layer is disposed between the electrode layer and the medicament-containing layer, said water supplying layer being composed of a water-containing self adhesive layer and a water-containing layer, and further a sealing cover is formed at the outside of the electrode layer.

3. The plaster structural assembly as claimed in claim 2, wherein the thickness of the medicament-containing layer is from 0.1 mm to 1.0 mm.

4. The plaster structural assembly as claimed in claim 8 wherein the medicament-containing layer is from about ½ to about ⅓ of the area of said water-containing self adhesive layer.

5. A method for administering a medicament to a subject in need of such medicament by absorption of said medicament by iontophoresis, said method comprising contacting the skin of said subject with the plaster structural assembly of claim 2 and thereafter applying an electric current.

* * * * *